United States Patent
Otto et al.

(10) Patent No.: US 11,147,823 B2
(45) Date of Patent: Oct. 19, 2021

(54) PHOSPHOLIPID ETHER ANALOGS FOR IMAGING AND TARGETED TREATMENT OF PEDIATRIC SOLID TUMORS

(71) Applicant: Wisconsin Alumni Research Foundation, Madison, WI (US)

(72) Inventors: Mario Otto, Fitchburg, WI (US); Dana C. Baiu, Madison, WI (US); Bryan P. Bednarz, Madison, WI (US); Jamey Paul Weichert, Fitchburg, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 8 days.

(21) Appl. No.: 15/647,557

(22) Filed: Jul. 12, 2017

(65) Prior Publication Data
US 2018/0015113 A1    Jan. 18, 2018

Related U.S. Application Data

(60) Provisional application No. 62/361,888, filed on Jul. 13, 2016.

(51) Int. Cl.
| | |
|---|---|
| *A61K 31/685* | (2006.01) |
| *A61K 33/18* | (2006.01) |
| *G01N 33/574* | (2006.01) |
| *A61K 31/69* | (2006.01) |
| *A61K 31/6615* | (2006.01) |

(52) U.S. Cl.
CPC ........ *A61K 31/685* (2013.01); *A61K 31/6615* (2013.01); *A61K 31/69* (2013.01); *A61K 33/18* (2013.01); *G01N 33/57407* (2013.01); *G01N 33/57484* (2013.01)

(58) Field of Classification Search
CPC .. A61K 31/685; A61K 31/6615; A61K 31/69; A61K 33/18; G01N 33/57407; G01N 33/57484
See application file for complete search history.

(56) References Cited

U.S. PATENT DOCUMENTS

| | | | | |
|---|---|---|---|---|
| 6,255,519 | B1 * | 7/2001 | Counsell | A61K 51/0408 |
| | | | | 558/166 |
| 8,535,641 | B2 * | 9/2013 | Weichert | A61K 51/04 |
| | | | | 424/1.11 |
| 8,877,159 | B2 * | 11/2014 | Weichert | A61K 51/04 |
| | | | | 424/1.11 |
| 9,339,564 | B2 * | 5/2016 | Weichert | A61K 51/0489 |
| 9,550,002 | B2 * | 1/2017 | Weichert | A61K 51/04 |
| 10,004,818 | B2 * | 6/2018 | Weichert | A61K 45/06 |
| 10,736,949 | B2 * | 8/2020 | Weichert | A61K 39/39 |
| 2014/0030187 | A1 | 1/2014 | Weichert et al. | |

OTHER PUBLICATIONS

Shukla et al. Clin Cancer Res; 18(3) Feb. 1, 2012 (Year: 2012).*
Roberta Marino et al., "Tumor-selective anti-cancer effects of the synthetic alkyl phosphocholine analog CLR1404 in neuroblastoma," Am J Cancer Res, vol. 5, No. 11, Nov. 1, 2015, pp. 3422-3435.
Nancy E. Kline, Nicole Sevier, "Solid Tumors in Children," Journal of Pediatric Nursing, vol. 18, No. 2, Apr. 1, 2003, pp. 96-102.

* cited by examiner

*Primary Examiner* — Kortney L. Klinkel
*Assistant Examiner* — William Y Lee
(74) *Attorney, Agent, or Firm* — Boyle Fredrickson S.C.

(57) ABSTRACT

It is disclosed herein that that certain alkylphosphocholine analogs are preferentially taken up by malignant pediatric tumor cells. The alkylphophocholine analogs are compounds having the formula:

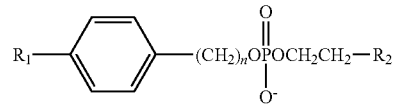

or salts thereof, wherein n is an integer from 12 to 24; and $R_2$ is $-N^+(CH_3)_3$. The compounds can be used to treat pediatric solid tumors or to detect pediatric solid tumors. In therapeutic treatment, $R_1$ includes a radioactive iodine isotope that locally delivers therapeutic dosages of radiation to the malignant pediatric tumor cells that preferentially take up the compound. In detection/imaging applications, $R_1$ includes a detection moiety, such as a fluorophore or a radioactive iodine isotope.

7 Claims, 10 Drawing Sheets
(1 of 10 Drawing Sheet(s) Filed in Color)

CLR1502

PHOSPHOLIPID ETHER ANALOGS FOR IMAGING AND TARGETED TREATMENT OF PEDIATRIC SOLID TUMORS

CROSS-REFERENCE TO RELATED APPLICATIONS

This application claims the benefit of U.S. Provisional Application No. 62/361,888, filed Jul. 13, 2016, which is incorporated by reference herein in its entirety.

STATEMENT REGARDING FEDERALLY SPONSORED RESEARCH OR DEVELOPMENT

This invention was made with government support under CA198392 awarded by the National Institutes of Health. The government has certain rights in the invention.

FIELD OF THE DISCLOSURE

This disclosure relates generally to disease treatment and medical diagnosis/imaging. In particular, the disclosure is directed to the use of alkyphosphocholine analogs to target and treat malignant pediatric solid tumors, and to related methods of detecting/imaging malignant pediatric solid tumor cells.

BACKGROUND

Pediatric solid tumors make up about 30% of all cancers (malignancies) occurring in children, and they can also occur rarely in adults. Commonly occurring malignant pediatric solid tumors include, without limitation, neuroblastoma (NB), Ewings sarcoma (EWS), rhabdomyosarcoma (RMS), osteosarcoma (OS), retinoblastoma (RB) and Wilms' tumor (WT) (see Kline, N E, Sevier, N. Solid Tumors in Children. Journal of Pediatric Nursing 2003; 18(2): 96-102).

Patients with refractory or relapsed malignant pediatric solid tumors face a dismal prognosis. For instance, the chance of cure for high-risk neuroblastoma is approximately 50% and less than 15% after relapse. For children with primary or relapsed metastatic rhabdomyosarcoma, the survival rate is less than 25%. Patients with recurrent Ewings sarcoma have an overall survival of less than 10%. Similarly miserable survival rates are reported for the majority of other therapy-refractory or relapsed malignant pediatric solid tumors.

Pediatric cancers are fundamentally different from adult cancers. Practically all pediatric solid tumors are classified as orphan diseases, and pediatric cancers that are also diagnosed in adults, such as osteosarcoma and Ewings sarcoma, are molecularly distinct from their adult counterparts, often having different clinical presentation and outcome, even in the face of highly aggressive multimodality therapy approaches. Thus, there is a need for novel, targeted therapies specifically for treating malignant pediatric solid tumors.

Many pediatric solid tumors are radiosensitive, but unfortunately, many such tumors tend to develop distant, widely disseminated metastases that make external beam radiation therapy impossible without damaging healthy, vital tissue. Therefore, radioactively labeled drugs that can be injected in the veins and specifically find and target cancer cells regardless where located in the body (molecularly targeted radiotherapy or MRT) may be of tremendous value in treating malignant pediatric solid tumors.

131I-MIBG ($I^{131}$-labeled-metaiodobenzylguanidine) is currently the only well-studied and established tumor-targeting radioactive agent in pediatric oncology, but it is mostly used in the palliative care setting and only targets neuroblastoma. In about 10% of cases 131I-MIBG is not taken up by neuroblastoma tumors at all. Unfortunately, for other challenging pediatric cancers, such as rhabdomyosarcoma, osteosarcoma and Ewing sarcoma, effective targeted radiotherapy does not exist at all.

Figure 1:
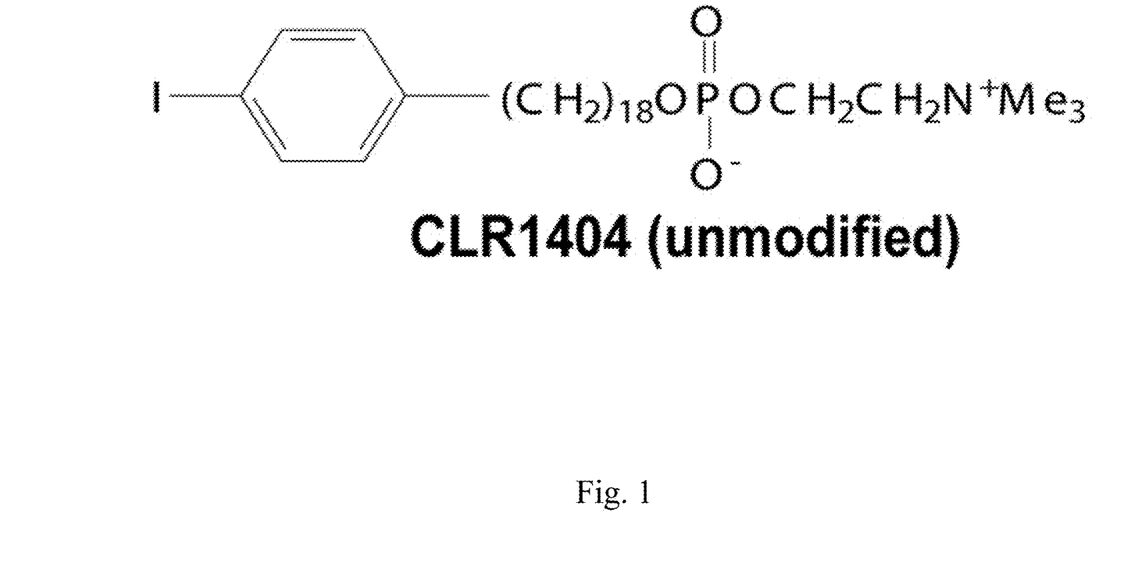
FIG. 1 shows the chemical structure of the base compound 18-(p-iodophenyl)octadecyl phosphocholine (CLR1404).

It has previously been shown that alkylphosphocholine analogs are preferentially taken up and retained by malignant adult solid tumor (i.e., adult solid tumor cancer) cells. In U.S. Patent Publication No. 2014/0030187, which is incorporated by reference herein in its entirety, Weichert et al. disclose using analogs of the base compound 18-(p-iodophenyl)octadecyl phosphocholine (CLR1404; see FIG. 1) for detecting and locating, as well as for treating, adult solid tumor cancers. For example, if the iodo moiety is an imaging-optimized radionuclide, such as iodine-124 ($[^{124}I]$—CLR1404), the analog can be used in positron emission tomography—computed tomography (PET/CT) or single-photon emission computed tomography (SPECT) imaging of adult solid tumors. Alternatively, if the iodo moiety is a radionuclide optimized for delivering therapeutic doses of radiation to the solid tumors cells in which the analog is taken up, such as iodine-125 or iodine-131 ($[^{125}I]$—CLR1404 or $[^{131}I]$—CLR1404), the analog can be used to treat the adult solid tumors.

Figure 2:
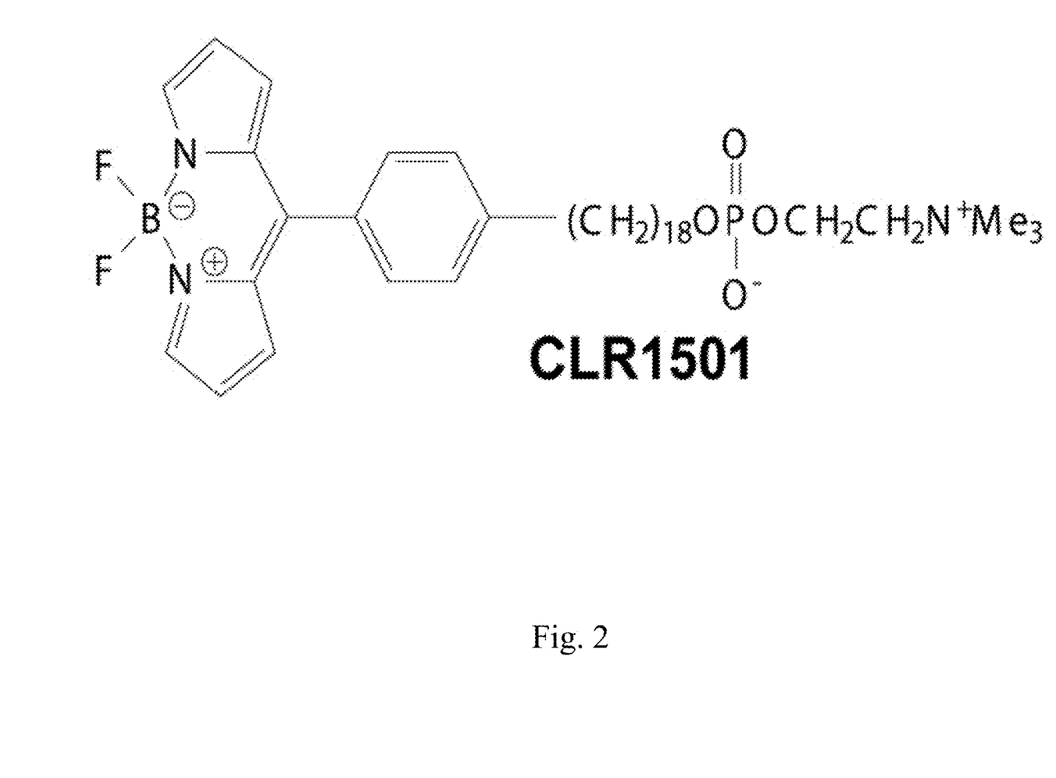
FIG. 2 shows the chemical formula of CLR1501, which is an analog of CLR1404 wherein the iodo moiety is substituted with a fluorescent boron-dipyrromethene (BODIPY) core (4,4-difluoro-4-bora-3a,4a-diaza-s-indacene).
Figure 3:
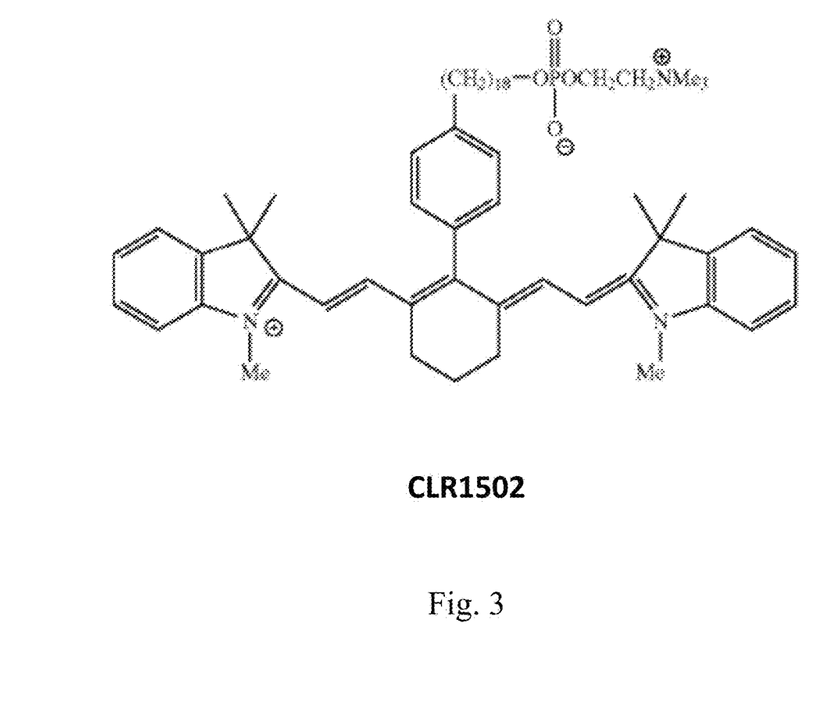
FIG. 3 shows the chemical formula of CLR1502, which is an analog of CLR1404 wherein the iodo moiety is substituted with the fluorophore IR-775.

In U.S. Patent Publication No. 2010/0284929, which is incorporated by reference herein in its entirety, Pinchuk et al. extend this idea to the visual detection of adult solid tumors. Specifically, Pinchuk et al. disclose further analogs of CLR1404, wherein the iodo moiety is substituted with a fluorophore. For example, if the iodo moiety is substituted with a boron-dipyrromethene (BODIPY) core (4,4-difluoro-4-bora-3a,4a-diaza-s-indacene), the resulting compound (CLR1501; see FIG. 2) is taken up by adult solid tumor cells, which can then be visually detected/imaged. CLR1404 analogs having other fluorophores substituted for the iodo moiety, such as IR-775 (CLR1502; see FIG. 3), can similarly be used to visually identify/detect adult solid tumors.

In contrast, before our work disclosed herein, no one had suggested or demonstrated that alkylphosphocholine analogs incorporating a radioactive iodine nuclide could be used to effectively treat one or more malignant pediatric solid tumors. Many critical and fundamental differences exist between pediatric and adult solid tumors that have long been known in the art. Because of these fundamental differences, the skilled artisan would not have expected that these previously disclosed methods of treating and/or imaging adult solid tumors could be successfully used to treat and/or image one or more pediatric solid tumors.

First, pediatric and adult solid tumors have distinct developmental origins. Pediatric cancers have an embryonal origin, i.e. are derived from early, feto-embryonal "developing" tissues. In contrast, adult solid tumors are derived from mature, epithelial tissues. This is reflected in a quite different composition of tumor types that are prevalent in children, but do not exist or are extremely rare in adults (such as retinoblastoma, neuroblastoma, rhabdomyosarcoma, nephroblastoma and the brain tumors medulloblastoma and atypical-teratoid rhabdoid tumor and many more). See Simone J V, Lyons J. The evolution of cancer care for children and adults. J Clin Oncol. 1998; 16(9): 2904-5.

Pediatric cancers are believed to develop from "programming errors" and faulty differentiation pathways on the way from pluripotent tissue stem cells to specific, mature tissue types. In contrast, adult cancers develop by virtue of the accumulation of losses in tumor suppressor genes and gains in proto-oncogenes and loss of related cell control mechanisms and are strongly influenced by environmental factors. This is in part reflected by (a) the distribution of cancers in the population, as cancer still (with exceptions) is a disease of the elderly, with more than half of all cancers diagnosed in patients older than 70 years (incidence of 450/100,000 per year), and (b) typical diagnoses such as breast cancer, colon cancer, prostate cancer and lung cancer—diseases that practically do not exist in children. Cancer in children is very rare, with an incidence of about 4/100,000 per year—less than 1% of all cancers diagnosed in the US.

Second, pediatric and adult solid tumors are genetically distinct. Genetic analyses of pediatric cancers demonstrate many differences when compared to adult cancers, making pediatric cancers distinct diseases. Even pediatric and adult cancers that, under the microscope, look the same, such as some leukemias or certain brain tumors are genetically different (see, e.g., Paugh B S, Qu C, Jones C, Liu Z, Adamowicz-Brice M, Zhang J, et al. Integrated molecular genetic profiling of pediatric high-grade gliomas reveals key differences with the adult disease (J Clin Oncol. 2010; 28(18):3061-8). Consequently, they require different treatment strategies and have completely different outcomes (see, e.g., Parsons D W, Li M, Zhang X, Jones S, Leary R J, Lin J C, et al. The genetic landscape of the childhood cancer medulloblastoma. Science. 2011; 331(2016): 435-9).

Accordingly, there is a need for new and effective methods of targeting therapies, particularly radiotherapies, to malignant pediatric solid tumors cells, and for new methods of detecting/imaging malignant pediatric solid tumor cells within a patient.

BRIEF SUMMARY

The inventors have determined that certain alkylphosphocholine analogs are preferentially taken up by malignant pediatric solid tumor cells, as compared to non-tumor cells. The inventors have further demonstrated that preferential uptake of such compounds can be used in the therapeutic treatment of malignant pediatric solid tumors, as well as in malignant pediatric solid tumor detection/imaging applications. In therapeutic treatment, the alkylphosphocholine targeting backbone includes a radioiodine isotope that locally delivers therapeutic dosages of radiation to the malignant pediatric solid tumor cells that preferentially take up the alkylphosphocholine analog. In detection/imaging applications, the alkylphosphocholine targeting backbone includes a detection moiety, such as a fluorophore or a radioactive iodine isotope.

Accordingly, in a first aspect, the disclosure encompasses a method of treating a malignant pediatric solid tumor in a subject having a malignant pediatric solid tumor. The method includes the step of administering to a subject an effective amount of a compound having the formula:

or a salt thereof, wherein $R_1$ comprises a radioactive iodine isotope; n is an integer from 12 to 24; and $R_2$ is $-N^+(CH_3)_3$.

In some embodiments, the radioactive iodine isotope is $^{123}I$, $^{125}I$ or $^{131}I$.

In some embodiments, n is 18. In some such embodiments, the radioactive iodine isotope is $^{123}I$, $^{125}I$ or $^{131}I$ (i.e., the compound is [$^{123}I$]—CLR1404, [$^{125}I$]—CLR1404 or [$^{131}I$]—CLR1404).

In some embodiments, the compound is administered by parenteral, intranasal, sublingual, rectal, or transdermal delivery. In some such embodiments, the compound is administered intravenously.

In some embodiments, the subject is a human.

In some embodiments, the malignant pediatric solid tumor that is treated is neuroblastoma (NB), Ewings sarcoma (EWS), rhabdomyosarcoma (RMS), osteosarcoma (OS), retinoblastoma (RB), Wilms' tumor (WT), or a pediatric brain tumor.

In a second aspect, the disclosure encompasses a method for inhibiting the proliferation or growth of malignant pediatric solid tumor cells. The method includes the step of contacting one or more malignant pediatric solid tumor cells with an effective amount of a compound having the formula:

or a salt thereof, wherein $R_1$ comprises a radioactive iodine isotope; n is an integer from 12 to 24; and $R_2$ is $-N^+(CH_3)_3$.

In some embodiments, the radioactive iodine isotope is $^{123}I$, $^{125}I$ or $^{131}I$. In some such embodiments, the radioactive iodine isotope is $^{131}I$.

In some embodiments, n is 18. In some such embodiments, the radioactive iodine isotope is $^{123}I$, $^{125}I$ or $^{131}I$ (i.e., (i.e., the compound is [$^{123}I$]—CLR1404, [$^{125}I$]—CLR1404 or [$^{131}I$]—CLR1404).

In some embodiments, the method is performed in vivo, ex vivo, or in vitro.

In some embodiments, the malignant pediatric solid tumor cells are neuroblastoma (NB) cells, Ewings sarcoma (EWS) cells, rhabdomyosarcoma (RMS) cells, osteosarcoma (OS) cells, retinoblastoma (RB) cells, Wilms' tumor (WT) cells, or pediatric brain tumor cells.

In a third aspect, the disclosure encompasses a method for detecting or imaging one or more malignant pediatric solid tumor cells in a biological sample. The method includes the steps of (a) contacting the biological sample with a compound having the formula:

or a salt thereof, wherein $R_1$ comprises a radioactive iodine isotope or a fluorophore; n is an integer from 12 to 24; and $R_2$ is $-N^+(CH_3)_3$, whereby the compound is differentially taken up by malignant pediatric solid tumor cells within the biological sample; and (b) identifying individual cells or regions within the biological sample that are emitting signals characteristic of the radioactive iodine isotope or fluorophore, whereby one or more malignant pediatric solid tumor cells are detected or imaged.

In some embodiments, $R_1$ is a fluorophore, and the signals characteristic of the fluorophore comprise optical signals. In some such embodiments, the fluorophore is BODIPY or IR-775. In some such embodiments, the compound is CLR1501 or CLR1502.

In some embodiments, the radioactive iodine isotope is $^{123}$I, $^{124}$I, $^{125}$I or $^{131}$I.

In some embodiments, n is 18. In some such embodiments, the compound is [$^{124}$I]—CLR1404.

In some embodiments, the step of identifying individual cells or regions within the biological sample that are emitting signals characteristic of the radioactive iodine isotope or fluorophore is performed by positron emission tomography (PET) imaging, single-photon emission computed tomography (SPECT) imaging, gamma camera planar imaging, or Cerenkov luminescence imaging.

In some embodiments, the malignant pediatric solid tumor cells are neuroblastoma (NB) cells, Ewings sarcoma (EWS) cells, rhabdomyosarcoma (RMS) cells, osteosarcoma (OS) cells, retinoblastoma (RB) cells or Wilms' tumor (WT) cells, or pediatric brain tumor cells.

In some embodiments, the biological sample is part or all of a subject. In some embodiments, the biological sample is obtained from a subject. In some such embodiments, the subject is a human.

In a fourth aspect, the disclosure encompasses a method of diagnosing a malignant pediatric solid tumor in a subject. The method includes the steps of performing the detection or imaging as described above, wherein the biological sample is obtained from, part of, or all of a subject. If malignant pediatric solid tumor cells are detected or imaged by the method, the subject is diagnosed with a malignant pediatric solid tumor.

Other objects, features and advantages of the present invention will become apparent after review of the specification, claims and drawings.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 4 is a bar graph illustrating the preferential uptake of CLR1501, a fluorescent derivative of CLR1404, by pediatric solid cancer cells (rhabdomyosarcoma Rd, Rh-41; Ewing's sarcoma TC-71, TC-106; neuroblastoma SK—N—AS, NB1691; osteosarcoma SAOS-2; glioblastoma SJ-GBM2), and for reference, the adult cancer cell lines PC3 and MT-330, compared to normal human fibroblasts (HUFI), by flow cytometry. Mean±standard error (SE) from minimum 3 experiments per cell line, *$P \leq 0.01$. MFI, mean fluorescence intensity; RMS, rhabdomyosarcoma; EWS, Ewing's sarcoma; NB, neuroblastoma; OS, osteosarcoma; GB, glioblastoma, PC, prostate adenocarcinoma. Cells were plated at $5 \times 10^5$ cells/ml in triplicates in media containing 5 μM CLR1501 (fluorescent CLR1404). Mean fluorescence intensity corrected for auto-fluorescence was averaged from three experiments±standard deviation. Compared to normal cells, all tumor cell uptake was significantly higher.

DETAILED DESCRIPTION

I. In General

It is understood that this disclosure is not limited to the particular methodology, protocols, materials, and reagents described, as these may vary. The terminology used herein is for the purpose of describing particular embodiments only, and is not intended to limit the scope of the present invention, which will be limited only by any later-filed nonprovisional applications.

As used herein and in the appended claims, the singular forms "a", "an", and "the" include plural reference unless the context clearly dictates otherwise. As well, the terms "a" (or "an"), "one or more" and "at least one" can be used interchangeably herein. The terms "comprising" and variations thereof do not have a limiting meaning where these terms appear in the description and claims. Accordingly, the terms "comprising", "including", and "having" can be used interchangeably.

Unless defined otherwise, all technical and scientific terms used herein have the same meanings as commonly understood by one of ordinary skill in the art to which this invention belongs. Although any methods and materials similar or equivalent to those described herein can be used in the practice or testing of the present invention, the preferred methods and materials are now described. All publications and patents specifically mentioned herein are incorporated by reference for all purposes including describing and disclosing the chemicals, instruments, statistical analysis and methodologies which are reported in the publications which might be used in connection with the invention. All references cited in this specification are to be taken as indicative of the level of skill in the art.

The terminology as set forth herein is for description of the embodiments only and should not be construed as limiting of the invention as a whole. Unless otherwise specified, "a," "an," "the," and "at least one" are used interchangeably and mean one or more than one.

The disclosure is inclusive of the compounds described herein (including intermediates) in any of their pharmaceutically acceptable forms, including isomers (e.g., diastereomers and enantiomers), tautomers, salts, solvates, polymorphs, prodrugs, and the like. In particular, if a compound is optically active, the invention specifically includes each of the compound's enantiomers as well as racemic mixtures of the enantiomers. It should be understood that the term "compound" includes any or all of such forms, whether explicitly stated or not (although at times, "salts" are explicitly stated).

"Pharmaceutically acceptable" as used herein means that the compound or composition or carrier is suitable for administration to a subject to achieve the treatments described herein, without unduly deleterious side effects in light of the necessity of the treatment.

The term "effective amount," as used herein, refers to the amount of the compounds or dosages that will elicit the biological or medical response of a subject, tissue or cell that is being sought by the researcher, veterinarian, medical doctor or other clinician.

As used herein, "pharmaceutically-acceptable carrier" includes any and all dry powder, solvents, dispersion media, coatings, antibacterial and antifungal agents, isotonic agents, absorption delaying agents, and the like. Pharmaceutically-acceptable carriers are materials, useful for the purpose of administering the compounds in the method of the present invention, which are preferably non-toxic, and may be solid, liquid, or gaseous materials, which are otherwise inert and pharmaceutically acceptable, and are compatible with the compounds of the present invention. Examples of such carriers include, without limitation, various lactose, mannitol, oils such as corn oil, buffers such as PBS, saline, polyethylene glycol, glycerin, polypropylene glycol, dimethylsulfoxide, an amide such as dimethylacetamide, a protein such as albumin, and a detergent such as Tween 80, mono- and oligopolysaccharides such as glucose, lactose, cyclodextrins and starch.

The term "administering" or "administration," as used herein, refers to providing the compound or pharmaceutical composition of the invention to a subject suffering from or at risk of the diseases or conditions to be treated or prevented.

A route of administration in pharmacology is the path by which a drug is taken into the body. Routes of administration may be generally classified by the location at which the substance is applied. Common examples may include oral and intravenous administration. Routes can also be classified based on where the target of action is. Action may be topical (local), enteral (system-wide effect, but delivered through the gastrointestinal tract), or parenteral (systemic action, but delivered by routes other than the GI tract), via lung by inhalation.

A topical administration emphasizes local effect, and substance is applied directly where its action is desired. Sometimes, however, the term topical may be defined as applied to a localized area of the body or to the surface of a body part, without necessarily involving target effect of the substance, making the classification rather a variant of the classification based on application location. In an enteral administration, the desired effect is systemic (non-local), substance is given via the digestive tract. In a parenteral administration, the desired effect is systemic, and substance is given by routes other than the digestive tract.

Non-limiting examples for topical administrations may include epicutaneous (application onto the skin), e.g., allergy testing or typical local anesthesia, inhalational, e.g. asthma medications, enema, e.g., contrast media for imaging of the bowel, eye drops (onto the conjunctiva), e.g., antibiotics for conjunctivitis, ear drops, such as antibiotics and corticosteroids for otitis externa, and those through mucous membranes in the body.

Enteral administration may be administration that involves any part of the gastrointestinal tract and has systemic effects. The examples may include those by mouth (orally), many drugs as tablets, capsules, or drops, those by gastric feeding tube, duodenal feeding tube, or gastrostomy, many drugs and enteral nutrition, and those rectally, various drugs in suppository.

Examples of parenteral administrations may include intravenous (into a vein), e.g. many drugs, total parenteral nutrition intra-arterial (into an artery), e.g., vasodilator drugs in the treatment of vasospasm and thrombolytic drugs for treatment of embolism, intraosseous infusion (into the bone marrow), intra-muscular, intracerebral (into the brain parenchyma), intracerebroventricular (into cerebral ventricular system), intrathecal (an injection into the spinal canal), and subcutaneous (under the skin). Among them, intraosseous infusion is, in effect, an indirect intravenous access because the bone marrow drains directly into the venous system. Intraosseous infusion may be occasionally used for drugs and fluids in emergency medicine and pediatrics when intravenous access is difficult.

As used herein, the term "intraperitoneal injection" or "IP injection" refers to the injection of a substance into the peritoneum (body cavity). IP injection is more often applied to animals than to humans. In general, IP injection may be preferred when large amounts of blood replacement fluids are needed, or when low blood pressure or other problems prevent the use of a suitable blood vessel for intravenous injection.

II. THE INVENTION

In certain aspects, the disclosure is directed to the use of fluorescently labeled alkylphosphocholine analogs or alkylphosphocholine analogs labeled with a radioactive iodine isotope for medical detection or detection/imaging of malignant pediatric tumor cells in a subject or in a biological sample. In other aspects, the disclosure is directed to the use of alkylphosphocholine analogs labeled with a radioactive iodine isotope to treat malignant pediatric tumors in a subject.

As noted in the background section, because of the substantial differences between adult and pediatric solid tumors that are well-known in the art, methods of treatment and imaging that may be used in the context of treating adult solid tumors would not be expected to work with pediatric solid tumors. The differences between pediatric and adult cancers extends specifically to the uptake mechanisms of alkylphosphocholine analogs, particularly in the context of CLR1404 and its derivatives. For instance, Weichert et al. have demonstrated in adult cancers that uptake of CLR1404 into the cell is dependent on lipid raft content of the plasma membrane (Weichert J P, Clark P A, Kandela I K, Vaccaro A M, Clarke W, Longino M A, et al. Alkylphosphocholine analogs for broad-spectrum cancer imaging and therapy. Sci Transl Med. 2014; 6(240):240ra75). In contrast, we have demonstrated that in a variety of neuroblastoma cell lines (neuroblastoma is the most common extra-cranial solid tumor of childhood), the uptake of CLR1404 into cells does not correlate with the density of lipid rafts (Marino R, Baiu D C, Bhattacharya S, Titz B, Hebron E, Menapace B D, et al. Tumor-selective anti-cancer effects of the synthetic alkyl phosphocholine analog CLR1404 in neuroblastoma. Am J Cancer Res. 2015; 5(11):3422-35).

In the context of the known differences between pediatric solid tumors and adult solid tumors, the results reported in this application were unexpected and surprising.

A. Radioactive Iodine Isotopes for Malignant Pediatric Solid Tumor Treatment

For the disclosed methods of therapeutically treating malignant pediatric solid tumors, any radioactive iodine isotope known to emit ionizing radiation in a form that would result in the death of cells that take up the analogs labeled with the radioactive iodine isotope can be incorporated into the alkylphosphocholine targeting backbone. In some embodiments, the radioactive iodine isotope emits its ionizing radiation in a form that minimizes damage to tissue outside of the cells that take up the labeled analogs.

In one non-limiting example, the incorporated radioactive iodine isotope is iodine-131. Iodine-131, which emits therapeutically effective beta and gamma radiation, has been used with great efficacy in the targeted treatment of thyroid cancer. In another non-limiting example, the radioactive iodine isotope may be iodine-125, which has the advantage of emitting low-energy gamma/X-ray irradiation Auger electrons, all of which act at a very limited treatment distance, thus sparing surrounding healthy tissue from radiation exposure. In yet another non-limiting example, the radioactive iodine isotope used is iodine-123.

B. Fluorescent Labels for Malignant Pediatric Solid Tumor Detection/Imaging

For the disclosed methods of detecting/imaging, any fluorophore known to emit optical signals in a form that is readily detectable by conventional optical imaging means may be incorporated into the targeting backbone. Non-limiting examples of "conventional imaging means" include, without limitation, fluorescence microscopy, flow cytometry, endoscopy, and preclinical near infrared fluorescence imaging. Non-limiting examples of fluorophores that could be incorporated include BODIPY and IR-775.

C. Radioactive Iodine Isotopes for Malignant Pediatric Solid Tumor Detection/Imaging For the disclosed methods of detecting/imaging malignant pediatric solid tumors, any radioactive iodine isotope known to emit radiation in a form that is readily detectable by conventional imaging means can be incorporated into the targeting backbone. Non-limiting examples of "conventional imaging means" include gamma ray detection, PET scanning, and SPECT scanning. Non-limiting examples of radioactive iodine isotopes that could be used include iodine-123, iodine-124, iodine-125, and iodine-131.

D. Methods of Synthesizing the disclosed analogs

The alkylphosphocholine analogs used in the disclosed methods are known in the art, as are methods of synthesizing such analogs. For details regarding synthetic materials and methods, see, e.g., U.S. Patent Publication Nos. 2010/0284929, 2010/0316567, 2012/0128596, 2014/0030187, and 2014/0023587, each of which is incorporated by reference herein in its entirety.

E. In Vitro Use of Optical Compounds

The disclosed compounds comprising a fluorophore (optical compounds) can be used in a variety of detection methods, including, for example, in endoscopic examination and detection. Such compounds may also be used for in vitro detection of malignant pediatric solid tumor cells, as illustrated in more detail in the Examples below.

F. Dosage Forms and Administration Methods

Any route of administration may be suitable for administering the disclosed alkylphosphocholine analogs to a subject. In one embodiment, the disclosed alkylphosphocholine analogs may be administered to the subject via intravenous injection. In another embodiment, the disclosed alkylphosphocholine analogs may be administered to the subject via any other suitable systemic deliveries, such as parenteral, intranasal, sublingual, rectal, or transdermal administrations.

In another embodiment, the disclosed alkylphosphocholine analogs may be administered to the subject via nasal systems or mouth through, e.g., inhalation.

In another embodiment, the disclosed alkylphosphocholine analogs may be administered to the subject via intraperitoneal injection or IP injection.

In certain embodiments, the disclosed alkylphosphocholine analogs may be provided as pharmaceutically acceptable salts. Other salts may, however, be useful in the preparation of the alkylphosphocholine analogs or of their pharmaceutically acceptable salts. Suitable pharmaceutically acceptable salts include, without limitation, acid addition salts which may, for example, be formed by mixing a solution of the alkylphosphocholine analog with a solution of a pharmaceutically acceptable acid such as hydrochloric acid, sulphuric acid, methanesulphonic acid, fumaric acid, maleic acid, succinic acid, acetic acid, benzoic acid, oxalic acid, citric acid, tartaric acid, carbonic acid or phosphoric acid.

Where the disclosed alkylphosphocholine analogs have at least one asymmetric center, they may accordingly exist as enantiomers. Where the disclosed alkylphosphocholine analogs possess two or more asymmetric centers, they may additionally exist as diastereoisomers. It is to be understood that all such isomers and mixtures thereof in any proportion are encompassed within the scope of the present disclosure.

The disclosure also includes methods of using pharmaceutical compositions comprising one or more of the disclosed alkylphosphocholine analogs in association with a pharmaceutically acceptable carrier. Preferably these compositions are in unit dosage forms such as tablets, pills, capsules, powders, granules, sterile parenteral solutions or suspensions, metered aerosol or liquid sprays, drops, ampoules, auto-injector devices or suppositories; for parenteral, intranasal, sublingual or rectal administration, or for administration by inhalation or insufflation.

For preparing solid compositions such as tablets, the principal active ingredient is mixed with a pharmaceutically acceptable carrier, e.g. conventional tableting ingredients such as corn starch, lactose, sucrose, sorbitol, talc, stearic acid, magnesium stearate, dicalcium phosphate or gums, and other pharmaceutical diluents, e.g. water, to form a solid preformulation composition containing a homogeneous mixture for a compound of the present invention, or a pharmaceutically acceptable salt thereof. When referring to these preformulation compositions as homogeneous, it is meant that the active ingredient is dispersed evenly throughout the composition so that the composition may be easily subdivided into equally effective unit dosage forms such as tablets, pills and capsules. This solid pre-formulation composition is then subdivided into unit dosage forms of the type described above containing from 0.1 to about 500 mg of the active ingredient of the present invention. Typical unit dosage forms contain from 1 to 100 mg, for example, 1, 2, 5, 10, 25, 50 or 100 mg, of the active ingredient. The tablets or pills of the novel composition can be coated or otherwise compounded to provide a dosage affording the advantage of prolonged action. For example, the tablet or pill can comprise an inner dosage and an outer dosage component, the latter being in the form of an envelope over the former. The two components can be separated by an enteric layer which, serves to resist disintegration in the stomach and permits the inner component to pass intact into the duodenum or to be delayed in release. A variety of materials can be used for such enteric layers or coatings, such materials including a number of polymeric acids and mixtures of polymeric acids with such materials as shellac, cetyl alcohol and cellulose acetate.

The liquid forms in which the alkylphosphocholine analogs may be incorporated for administration orally or by injection include aqueous solutions, suitably flavored syrups, aqueous or oil suspensions, and flavored emulsions with edible oils such as cottonseed oil, sesame oil, coconut oil or peanut oil, as well as elixirs and similar pharmaceutical vehicles. Suitable dispersing or suspending agents for aqueous suspensions include synthetic and natural gums such as tragacanth, acacia, alginate, dextran, sodium carboxymethylcellulose, methylcellulose, polyvinylpyrrolidone or gelatin.

The disclosed alkylphosphocholine analogs are particularly useful when formulated in the form of a pharmaceutical injectable dosage, including in combination with an injectable carrier system. As used herein, injectable and infusion dosage forms (i.e., parenteral dosage forms) include, but are not limited to, liposomal injectables or a lipid bilayer vesicle having phospholipids that encapsulate an active drug substance. Injection includes a sterile preparation intended for parenteral use.

Five distinct classes of injections exist as defined by the USP: emulsions, lipids, powders, solutions and suspensions. Emulsion injection includes an emulsion comprising a sterile, pyrogen-free preparation intended to be administered parenterally. Lipid complex and powder for solution injection are sterile preparations intended for reconstitution to form a solution for parenteral use. Powder for suspension injection is a sterile preparation intended for reconstitution to form a suspension for parenteral use. Powder lyophilized for liposomal suspension injection is a sterile freeze dried preparation intended for reconstitution for parenteral use that is formulated in a manner allowing incorporation of liposomes, such as a lipid bilayer vesicle having phospholipids used to encapsulate an active drug substance within a lipid bilayer or in an aqueous space, whereby the formulation may be formed upon reconstitution. Powder lyophilized for solution injection is a dosage form intended for the solution prepared by lyophilization ("freeze drying"), whereby the process involves removing water from products in a frozen state at extremely low pressures, and whereby subsequent addition of liquid creates a solution that conforms in all respects to the requirements for injections. Powder lyophilized for suspension injection is a liquid preparation intended for parenteral use that contains solids suspended in a suitable fluid medium, and it conforms in all respects to the requirements for Sterile Suspensions, whereby the medicinal agents intended for the suspension are prepared by lyophilization. Solution injection involves a liquid preparation containing one or more drug substances dissolved in a suitable solvent or mixture of mutually miscible solvents that is suitable for injection.

Solution concentrate injection involves a sterile preparation for parenteral use that, upon addition of suitable solvents, yields a solution conforming in all respects to the requirements for injections. Suspension injection involves a liquid preparation (suitable for injection) containing solid particles dispersed throughout a liquid phase, whereby the particles are insoluble, and whereby an oil phase is dispersed throughout an aqueous phase or vice-versa. Suspension liposomal injection is a liquid preparation (suitable for injection) having an oil phase dispersed throughout an aqueous phase in such a manner that liposomes (a lipid bilayer vesicle usually containing phospholipids used to encapsulate an active drug substance either within a lipid bilayer or in an aqueous space) are formed. Suspension sonicated injection is a liquid preparation (suitable for injection) containing solid particles dispersed throughout a liquid phase, whereby the particles are insoluble. In addition, the product may be sonicated as a gas is bubbled through the suspension resulting in the formation of microspheres by the solid particles.

The parenteral carrier system includes one or more pharmaceutically suitable excipients, such as solvents and co-solvents, solubilizing agents, wetting agents, suspending agents, thickening agents, emulsifying agents, chelating agents, buffers, pH adjusters, antioxidants, reducing agents, antimicrobial preservatives, bulking agents, protectants, tonicity adjusters, and special additives.

The following examples are offered for illustrative purposes only, and are not intended to limit the scope of the present invention in any way. Indeed, various modifications of the invention in addition to those shown and described herein will become apparent to those skilled in the art from the foregoing description and the following examples and fall within the scope of the appended claims.

III. EXAMPLES

Example 1

Selective In vitro Uptake of CLR1501 in Multiple Malignant Pediatric Solid Tumor Cell Lines In this example, we demonstrate that an analog of the base compound CLR1404 having a fluorophore substituted for the iodo moiety (CLR1501) exhibits high uptake in ten different malignant pediatric solid tumor cell lines, including three neuroblastoma cell lines (NB1691, SK—N—AS and CHLA-20), two rhabdomyosarcoma cell lines (Rd, Rh-41), an osteosarcoma cell line (SAOS-2), two Ewing sarcoma cell lines (TC-71 and TC-106, and a pediatric brain tumor (glioblastoma) cell line (SJ-GBM2). In contrast, we show that these analogs exhibit much less uptake in normal human pediatric fibroblast (HUFI) cells. Results for pediatric tumor cells were comparable to uptake in an adult brain tumor (glioblastoma) cell line (MT-300) and an adult prostate adenocarcinoma cell line (PC3).

Accordingly, this example demonstrates the potential of using analogs of CLR1404 incorporating a radioactive iodine moiety to specifically target localized radiation therapy to malignant pediatric tumor cells in a subject, or of using analogs of CLR1404 incorporating a detection moiety, such as a fluorophore or iodine radiolabel, to identify, detect, and/or image malignant pediatric solid tumor cells.

Each cell line ($5\times10^5$ cells/ml) was incubated for 16-19 hours with 5 µM CLR1501, then washed with 10% FBS medium for 4 hours. Cells were then measured by flow cytometry (FACSCalibur, BD Biosciences) and analyzed using FlowJo 8.2 (Tree Star, Ashland, Oreg.). Mean fluorescence intensity (MFI) per cell was corrected for autofluorescence (FL1 index) and averaged from three experiments±standard deviation.

Figure 4:
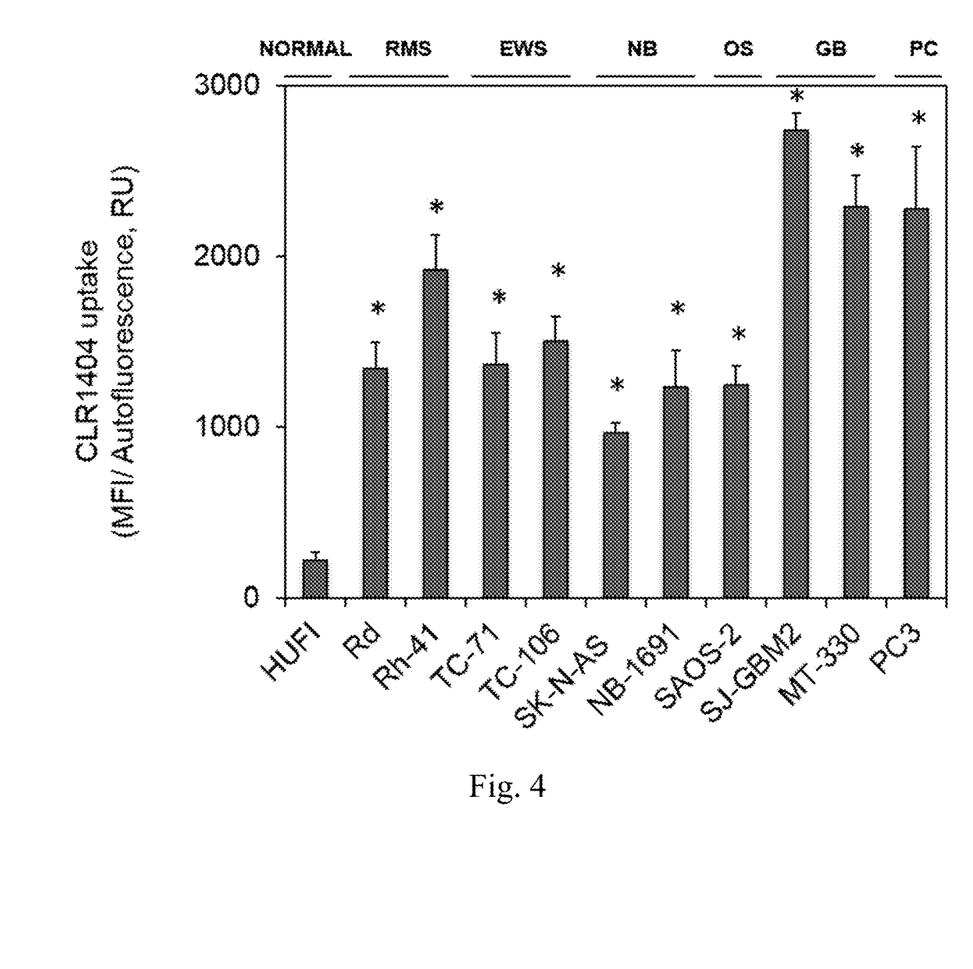

CLR1501 uptake in all the pediatric solid tumor cells tested was significantly higher than it was in normal pediatric fibroblast HUFI) cells. As shown in FIG. 4, the Rd, Rh-41, Tc-71, TC-106, SK—N—AS, NB-1691, SAOS-2, and SJ-GBM2 pediatric tumor cells lines exhibited increased CLR1501 uptake at $p<0.01$. The CHLA-20 neuroblastoma cells and the Rh-30 rhapdosarcoma cells also exhibited highly significant increases in CLR1501 uptake, as compared to the normal cells ($p<0.02$; data not shown).

Taken together, these results show that alkylphosphocholine analogs can be used to differentially target malignant pediatric solid tumor cells. The analogs can be designed as targeted agents for local delivery of radiation therapy by incorporating a radioactive iodine isotope, or for targeted delivery of detection/imaging moieties, by incorporating either a fluorophore or a radioactive iodine isotope.

Example 2

In vivo Uptake and Dosimetry of $^{124}$I—CLR1404 in Mice Xenografted with Four Different Pediatric Sold Tumor Types In this example, we demonstrate the differential uptake of $^{124}$I—CLR1404 in pediatric solid tumors in vivo, and its use in PET/CT imaging of such tumors. The PET/CT data was then used to predict the corresponding therapeutic dosages using $^{131}$I—CLR1404. The results were obtained using animal model systems for neuroblastoma, Ewing sarcoma and rhabdomyosarcoma.

Specifically, four mice were xenografted with one of four different pediatric tumor cell lines (CHLA-20 (neuroblastoma), NB-1691 (neuroblastoma), TC-71 (Ewing sarcoma), and Rh-30 (rhabdomyosarcoma). For each of the sixteen xenografted mice, 100 µl cell suspension containing $3\times10^6$ tumor cells (>95% viability, passage 5-25) was inoculated into subcutaneous tissue of the left flank of a 6-8 week-old NSG mouse (NOD.Cg-Prdc$^{scid}$Il2rg$^{tm1Wj1}$/SzJ, Jackson Laboratory, Bar Harbor, Me.). Once xenograft tumors measured a minimum of about $7\times7$ mm, the mice received $^{124}$I—CLR1404 at 8-13 µCi/g via tail vein injection. After an uptake period, PET/CT imaging was performed on the mice at 5 and 6 time-points. Following image acquisition, the images were reconstructed, co-registered, resampled, rescaled, and corrected for partial volume effects (PVE), and masked.

Figure 5:
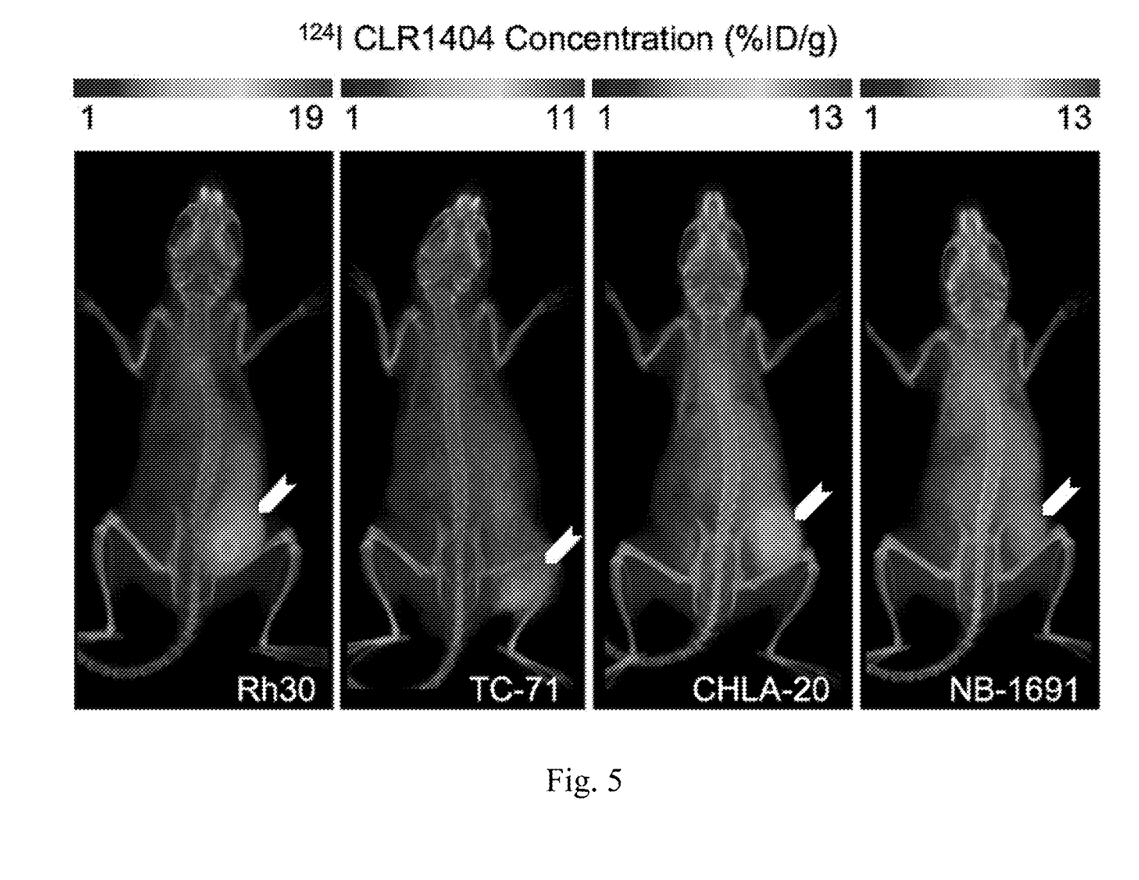
FIG. 5 includes representative coronal MicroPET/CT three-dimensional volume renderings of one representative NSG mouse of the four mice scanned for each of four xenografted tumor types (rhabdomyosarcoma Rh30; Ewing's sarcoma TC-71; neuroblastoma CHLA-20 and NB1691). The images are shown as colorwashes of tissue activity calculated as percent of injected dose/g tissue (% ID/g) in xenografts (arrowheads) and normal tissue of the NSG mice, 72 h after $^{124}$I—CLR-1404 administration.

All the scanned mice produced PET/CT three-dimensional volume renderings showing cumulative absorbed dose distribution concentrated in the xenografted tumor. Images are shown in FIG. 5 for a single representative of the Rh30, TC-71, CHLA-20, and NB-1691 xenografts. The results confirm the differential uptake of $^{124}$I—CLR1404 into the xenografted pediatric solid tumor tissue, and demonstrate the potential use of CLR1404 analogs incorporating radioactive iodine isotopes in the imaging and/or detection of malignant pediatric solid tumors or tumor cells.

Figure 6:
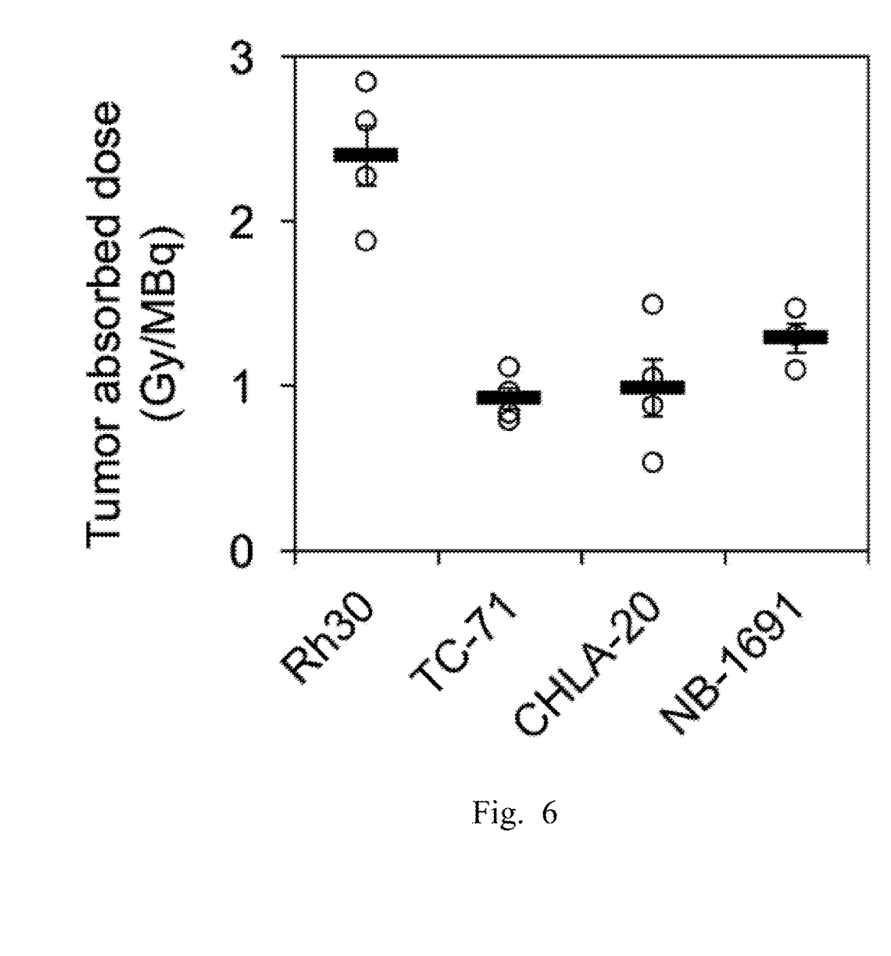
FIG. 6 is a graph showing calculated $^{131}$I—CLR-1404 absorbed dose per individual mouse xenograft (circles) and mean±SE (horizontal bar) for NSG mice with four different xenografted tumor types (rhabdomyosarcoma Rh30; Ewing's sarcoma TC-71; neuroblastoma CHLA-20 and NB1691). Each circle represents one mouse (n=4 for each tumor type).

The pre-treatment PET images of $^{124}$I—CLR1404 were used to predict potential therapeutic doses of $^{131}$I—CLR1404. The measured radioactivity of the $^{124}$I—CLR1404 was converted to the expected radioactivity of $^{131}$I—CLR1404 for each xenograft at each time point by assuming the same injection activity and accounting for the difference in physical decay rates. The tumors and normal tissues were contoured using anatomical and functional images. The CT and the PET images were used in the MC dose platform to define the geometry and source distribution, respectively. The calculated $^{131}$I—CLR1404 absorbed dose for each mouse and the mean for each xenograft type is shown in FIG. 6.

The CT images were used to define the material composition and mass density of the simulation geometry. CT's were co-registered to a single time point using normalized mutual information based affine CT-CT co-registration. The CT transformations were then applied to the PET at each time point.

Regions of interest (ROI) were segmented for the tumors and for healthy tissue (brain, cord, lungs, heart, kidneys, liver, bladder and marrow) based on axial slices of the CT data. Mean PET tracer uptake values and standard deviation of the CT-based ROIs were extracted using the Materials Statistics module. For each mouse, mean doses to healthy and tumor ROIs were calculated.

Figure 7:
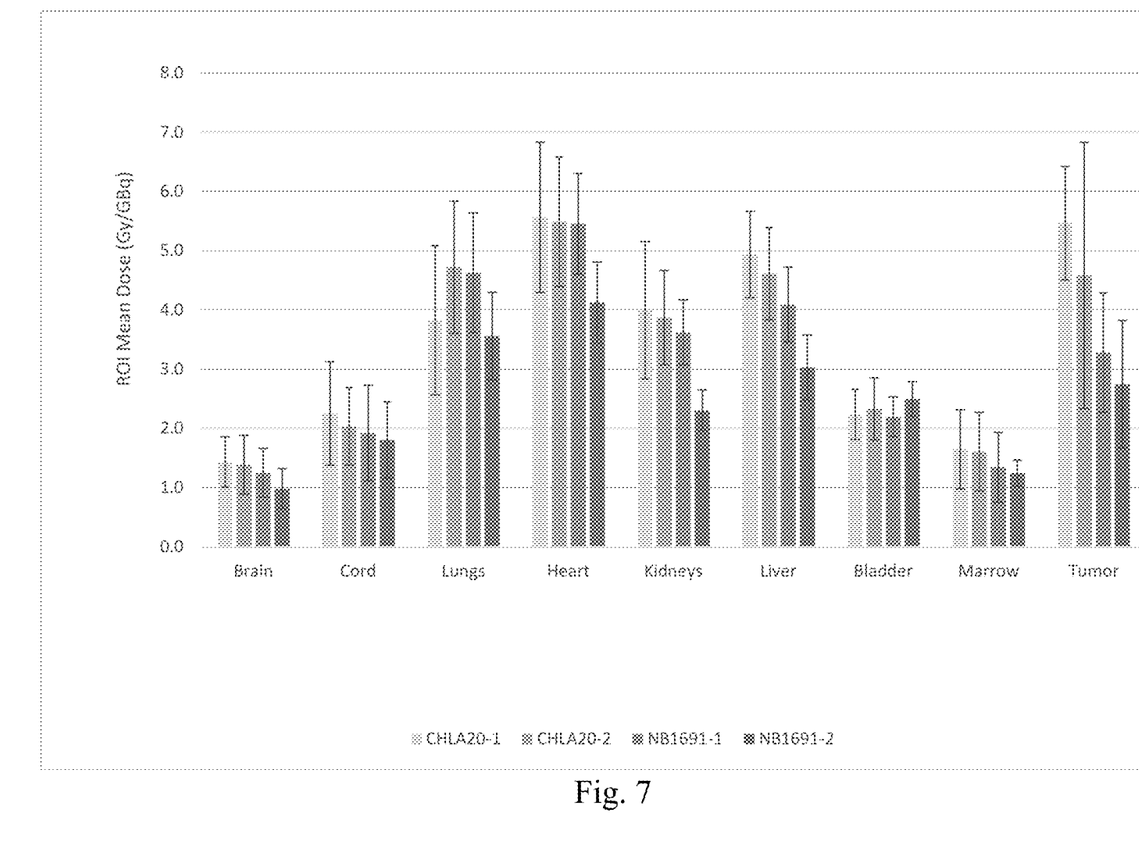
FIG. 7 is a bar graph illustrating mean doses to healthy ROIs and tumors in two CHLA-20 and two NB-1691 xenografted mice (representative).

FIG. 7 shows the results for two of the CHLA-20 xenografts (CHLA20-1 and CHLA20-2) and two of the NB-1691 xenografts (NB1691-1 and NB1691-2). The positive tumor to absorbed dose ratio (OAR) in the xenografted mice are similar to what has been reported in preclinical dosimetry studies of $^{131}$I-MIBG, which is currently the only established tumor-targeting radioactive agent used to treat malignant pediatric solid tumors.

Together, these results demonstrate that the disclosed methods can readily be applied to clinical pediatric solid tumor imaging applications, and illustrate the potential of the disclosed methods for treating pediatric solid tumors.

Example 3

Demonstrating Anti-Tumor Activity of [$^{131}$I]—CLR1404 In vivo Against Six Different Pediatric Solid Tumor Types In this example, we demonstrate the efficacy of the disclosed therapeutic strategy in mice xenografted with six distinct types of malignant pediatric solid tumors, including two different neuroblastomas (CHLA-20 and NB-1691), two different Ewings sarcomas (TC-71 and TC-106), a rhabdomyosarcoma (Rh30), and an osteosarcoma (SAOS-2).

Specifically, the analog [$^{131}$I]—CLR1404, which is differentially taken up and maintained in malignant pediatric solid tumor cells, contains the radionuclide iodine-131, a radioactive isotope of iodine that locally emits potentially therapeutic doses of beta and gamma radiation. After uptake into the targeted malignant pediatric solid tumor cells, the locally emitted radiation will differentially kill the malignant pediatric solid tumor cells that take up the analog. Such bioactivity against malignant pediatric solid tumors xenografted into mice is demonstrated in this example.

Rh30, TC-71, TC-106, CHLA-20, NB-1691, and SAOS-2 subcutaneous flank xenografts were induced in mice, as described in Example 2 above. Tumors were measured twice weekly with calipers, and the tumor volume was calculated. When tumors reached a volume of approximately 50 mm$^3$, mice were randomly assigned to receive either $^{131}$I—CLR1404 in doses of 3.5 µCi/g or an excipient (equimolar $^{127}$I—CLR1404), and measurement of tumor size continued. Survival rates as a function of time were also observed in the xenografted mice.

Figure 8:
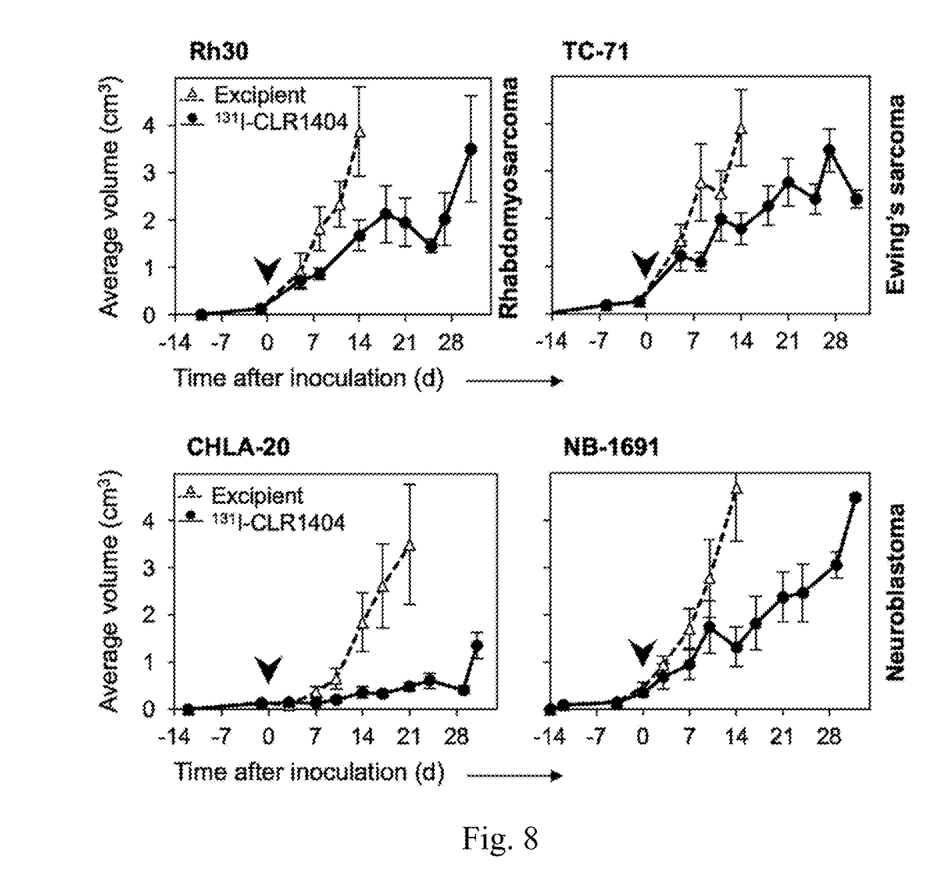
FIG. 8 includes graphs demonstrating the radiotherapeutic effect of $^{131}$I—CLR1404 in pediatric solid cancer xenograft NSG models (rhabdomyosarcoma Rh30; Ewing's sarcoma TC-71; neuroblastoma CHLA-20 and NB1691), versus excipient. Mean±SE tumor volumes for the duration of four $^{131}$I half-lives. Arrowhead designates start of treatment; d, days. Number of animals is detailed in Table 1.
Figure 9:
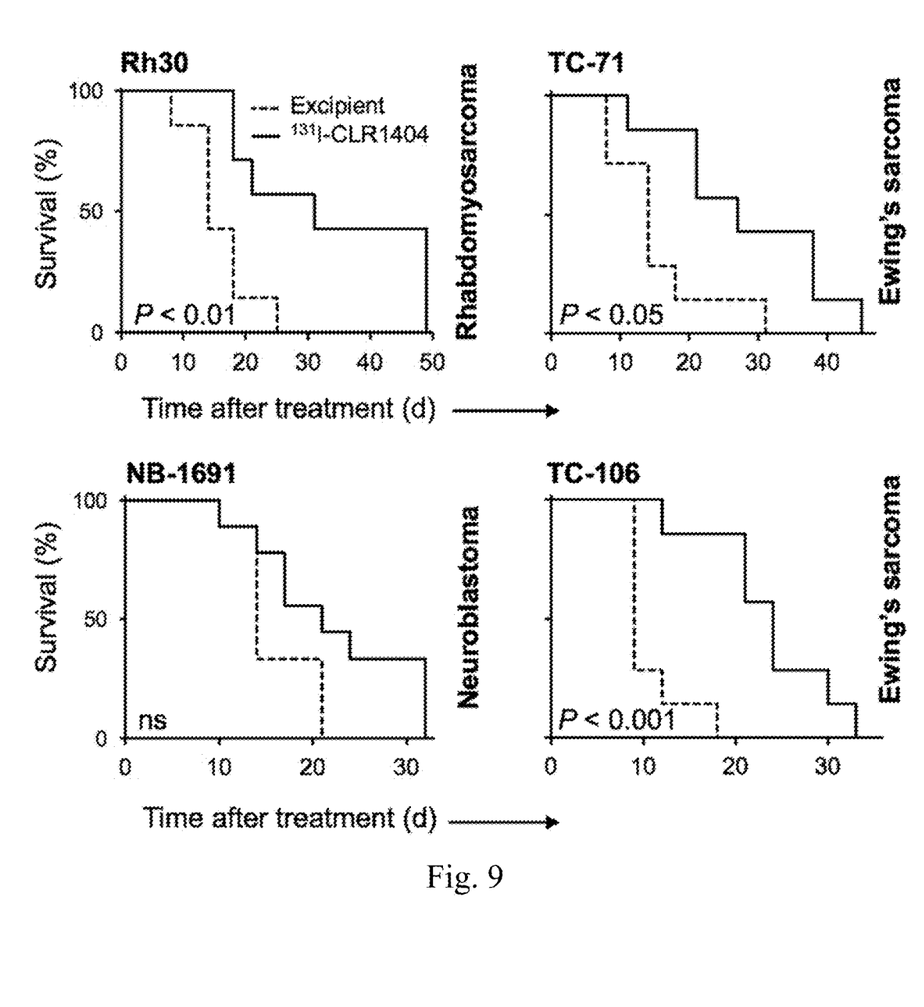
FIG. 9 includes graphs showing Kaplan-Meier survival analysis in four pediatric tumor xenograft models (rhabdomyosarcoma Rh30; Ewing's sarcoma TC-71, TC-106; neuroblastoma NB1691) after administration of $^{131}$I—CLR1404. D, days; ns, not significant. Number of animals is detailed in Table 1.
Figure 10:
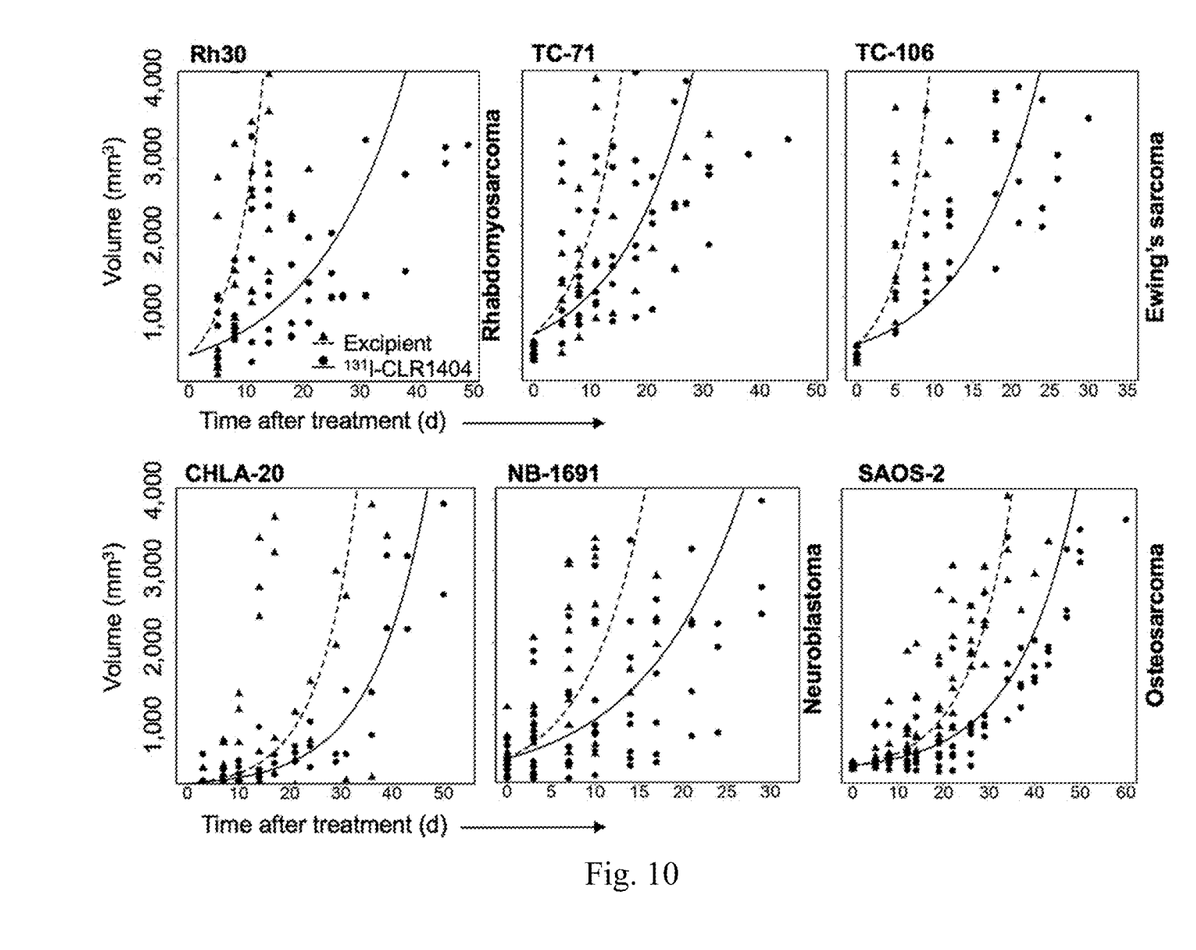
FIG. 10 includes graphs illustrating the radiotherapeutic effect of $^{131}$I—CLR1404 in pediatric solid cancer xenograft NSG models, versus excipient: linear mixed effects analysis of predicted growth rate (each symbol represents one mouse/time-point). D, days. Number of animals is detailed in Table 1.

As seen in FIG. 8-10, the results demonstrate that $^{131}$I—CLR1404 in doses of 3.5 µCi/g had a statistically significant in vivo therapeutic effect when compared with excipient, resulting in decreased mean tumor volumes (FIG. 8, shown for Rh30, TC-71, CHLA-20 and NB-1691), and slowing the growth rate of xenografts of human neuroblastoma (CHLA-20, NB-1691), rhabdomyosarcoma (Rh30), Ewing's sarcoma (TC-71 and TC-106), and osteosarcoma (SAOS-2) in immunodeficient mice (FIG. 10). The treatment with $^{131}$I—CLR1404 also extended animal survival with low toxicity in four groups, with the increased survival being statistically significant in Ewing's sarcoma and rhabdomyosarcoma xenografts (FIG. 9).

A linear mixed effects analysis of predicted growth rate was performed using the tumor size data described above. The results are shown in Table 1 below, and in graphical form in FIG. 10.

TABLE 1

Tumor Growth Rate Analysis Using a Linear Mixed Effects Model

| Xenograft | n animals/ experiment | n animals/ group | Slope log volume* | | P value† |
|---|---|---|---|---|---|
| | | | Excipient | $^{131}$I-CLR1404 | |
| Rh30 | 14 | 7 | 0.18 | 0.06 | <0.0001 |
| TC-71 | 14 | 7 | 0.14 | 0.08 | <0.0003 |
| TC-106 | 14 | 7 | 0.26 | 0 10 | <0 0001 |
| CHLA-20 | 12 | 6 | 0.13 | 0.09 | 0.0124 |
| NB-1691 | 18 | 9 | 0.15 | 0.09 | <0.0001 |
| SAOS-2 | 14 | 7 | 0.11 | 0.08 | <0.0001 |

*Prediction of the tumor growth rate (slope of the mixed model function, using logarithmic transformation of tumor volumes).
†Comparison between predicted tumor growth rates of excipient versus drug treatment group.

These results further demonstrate the efficacy of using the disclosed alkylphosocholine analogs to deliver targeted radiotherapy to effectively treat malignant pediatric solid tumors.

In sum, the data presented in the examples demonstrate that CLR1404 is selectively sequestered and retained in multiple pediatric cancer cell lines both in vitro and in in vivo. Furthermore, treatment of NSG mice bearing human neuroblastoma, rhabdomyosarcoma, Ewing's sarcoma and Osteosarcoma xenografts with single-dose $^{131}$I—CLR1404 led unequivocally to significant tumor growth rate reduction and survival benefit.

Taken together, the data disclosed throughout the examples demonstrate that CLR1404 and its analogs can be used to effectively target a broad range of pediatric solid tumors, either for local delivery of radiation therapy by incorporating a radioactive iodine isotope, or for targeted delivery of detection/imaging moieties, by incorporating either a fluorophore or a radioactive iodine isotope.

Other embodiments and uses of the invention will be apparent to those skilled in the art from consideration from the specification and practice of the invention disclosed herein. All references cited herein for any reason, including all journal citations and U.S./foreign patents and patent applications, are specifically and entirely incorporated herein by reference. It is understood that the invention is not confined to the specific reagents, formulations, reaction conditions, etc., herein illustrated and described, but embraces such modified forms thereof as come within the scope of the following claims.

The invention claimed is:

1. A method for treating a malignant pediatric solid tumor in a subject, comprising administering to a subject having a malignant pediatric solid tumor an effective amount of a compound having the formula:

or a salt thereof, wherein:
$R_1$ is a radioactive iodine isotope;
n is an integer from 12 to 24; and
$R_2$ is —N$^+$(CH$_3$)$_3$;
whereby the malignant pediatric solid tumor is a rhabdomyosarcoma (RMS) tumor treated in the subject.

2. The method of claim 1, wherein the radioactive iodine isotope is selected from the group consisting of $^{123}$I, $^{125}$I and $^{131}$I.

3. The method of claim 1, wherein n is 18, and the radioactive iodine isotope is $^{123}$I, $^{125}$I, or $^{131}$I (the compound is [$^{123}$I]—CLR1404, [$^{125}$I]—CLR1404 or [131I]—CLR1404).

4. The method of claim 1, wherein the compound is administered by parenteral, intranasal, sublingual, rectal, or transdermal delivery.

5. A method for inhibiting the proliferation or growth of malignant pediatric solid tumor cells, comprising contacting one or more malignant pediatric solid tumor cells with an effective amount of a compound having the formula:

or a salt thereof, wherein:
$R_1$ is a radioactive iodine isotope;
n is an integer from 12 to 24; and
$R_2$ is —N$^+$(CH$_3$)$_3$;
whereby growth or proliferation the malignant pediatric solid tumor cells is a rhabdomyosarcoma (RMS) tumor, wherein said tumor is inhibited.

6. The method of claim 5, wherein the radioactive iodine isotope is selected from the group consisting of $^{123}$I, $^{125}$I and $^{131}$I.

7. The method of claim 5, wherein n is 18, and the radioactive iodine isotope is $^{123}$I, $^{125}$I, or $^{131}$I (the compound is [$^{123}$I]—CLR1404, [$^{125}$I]—CLR1404 or [$^{131}$I]—CLR1404).

* * * * *